(12) United States Patent
Shiran et al.

(10) Patent No.: US 11,439,365 B2
(45) Date of Patent: Sep. 13, 2022

(54) METHOD AND SYSTEMS FOR PERIODIC IMAGING

(71) Applicant: GE Precision Healthcare LLC, Milwaukee, WI (US)

(72) Inventors: Carmit Shiran, Haifa (IL); Antonio Fabian Fermoso, Madrid (ES); Cynthia Owen, Powhatan, AR (US); Menachem Halmann, Monona, WI (US); Mor Vardi, Haifa (IL)

(73) Assignee: GE Precision Healthcare LLC, Milwaukee, WI (US)

( * ) Notice: Subject to any disclaimer, the term of this patent is extended or adjusted under 35 U.S.C. 154(b) by 459 days.

(21) Appl. No.: 16/513,558

(22) Filed: Jul. 16, 2019

(65) Prior Publication Data
US 2021/0015463 A1 Jan. 21, 2021

(51) Int. Cl.
*A61B 8/00* (2006.01)
*A61B 8/02* (2006.01)
*A61H 31/00* (2006.01)

(52) U.S. Cl.
CPC ............ *A61B 8/463* (2013.01); *A61B 8/02* (2013.01); *A61B 8/465* (2013.01); *A61H 31/005* (2013.01)

(58) Field of Classification Search
CPC ......... A61B 8/00; A61B 8/0883; A61B 8/463; A61B 8/465; A61H 31/005; A61H 1/001; A61H 1/005; A61H 1/006; A61H 1/008; A61H 2201/50; A61H 2201/5007; A61H 2201/501; A61H 2201/5023; A61H 2201/5025; A61H 2201/5043; A61H 2201/5046; A61H 2230/25; A61H 2230/255; A61H 2230/30; A61H 2230/40; G06T 2207/10132; G06T 2207/30048; G06T 2207/30101; G06T 7/0012; G06T 2207/30196; G09B 23/288; G09B 19/003; G09B 5/06; G09B 5/065; G09B 23/28; G09B 23/306; G09B 23/30; G09B 23/32
See application file for complete search history.

(56) References Cited

U.S. PATENT DOCUMENTS

| 5,976,088 A | 11/1999 | Urbano et al. |
| 6,350,238 B1 | 2/2002 | Olstad et al. |
| 8,715,188 B2 | 5/2014 | Willsie et al. |
| 2006/0079779 A1* | 4/2006 | Takimoto ............ G01S 7/52063 600/447 |

(Continued)

OTHER PUBLICATIONS

Feigenbaum, Harvey. "Digital echocardiography." The American journal of cardiology 86, No. 4A (2000): 2G-3G.*

*Primary Examiner* — Carolyn A Pehlke
(74) *Attorney, Agent, or Firm* — McCoy Russell LLP

(57) ABSTRACT

Various methods and systems for displaying cine loops during a periodic imaging session are disclosed. In one example, a method includes acquiring, with an ultrasound probe, a first set of images of an imaging subject during a first imaging period, displaying the first set of images as a first cine loop at a first display area of a display, acquiring, with the ultrasound probe, a second set of images of the imaging subject during a second imaging period different than the first imaging period, and displaying the second set of images as a second cine loop at a second display area of the display, different than the first area, while maintaining display of the first cine loop at the first display area.

15 Claims, 6 Drawing Sheets

(56) References Cited

U.S. PATENT DOCUMENTS

| | | | |
|---|---|---|---|
| 2006/0116578 A1 | 6/2006 | Grunwald et al. | |
| 2007/0016029 A1 | 1/2007 | Donaldson et al. | |
| 2010/0076960 A1* | 3/2010 | Sarkissian | G06F 16/9535 707/722 |
| 2011/0137169 A1* | 6/2011 | Akaki | G16H 30/40 600/443 |
| 2016/0143629 A1* | 5/2016 | Buckton | A61B 8/543 600/440 |
| 2016/0143804 A1* | 5/2016 | Nilsson | A61H 31/006 601/41 |
| 2018/0185240 A1* | 7/2018 | von Schenck | A61H 31/005 |
| 2019/0029919 A1* | 1/2019 | Suh | A61B 5/4836 |
| 2019/0192117 A1* | 6/2019 | Tashiro | A61B 8/5207 |
| 2019/0336101 A1* | 11/2019 | Chiang | G01S 7/52079 |

* cited by examiner

METHOD AND SYSTEMS FOR PERIODIC IMAGING

FIELD

Embodiments of the subject matter disclosed herein relate to ultrasound imaging.

BACKGROUND

Medical diagnostic ultrasound imaging systems typically include a set of imaging modes, such as a B mode and color flow Doppler mode. For B-mode imaging, the ultrasound imaging system generates a two-dimensional image of tissue in which the brightness of a pixel corresponds to the intensity of the echo return. During a period of time, a plurality of successive images may be saved for playback as short video clip, referred to as a cine loop.

BRIEF DESCRIPTION

In one embodiment, a method includes acquiring, with an ultrasound probe, a first set of images of an imaging subject during a first imaging period, displaying the first set of images as a first cine loop at a first display area of a display, acquiring, with the ultrasound probe, a second set of images of the imaging subject during a second imaging period different than the first imaging period, and displaying the second set of images as a second cine loop at a second display area of the display, different than the first area, while maintaining display of the first cine loop at the first display area.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
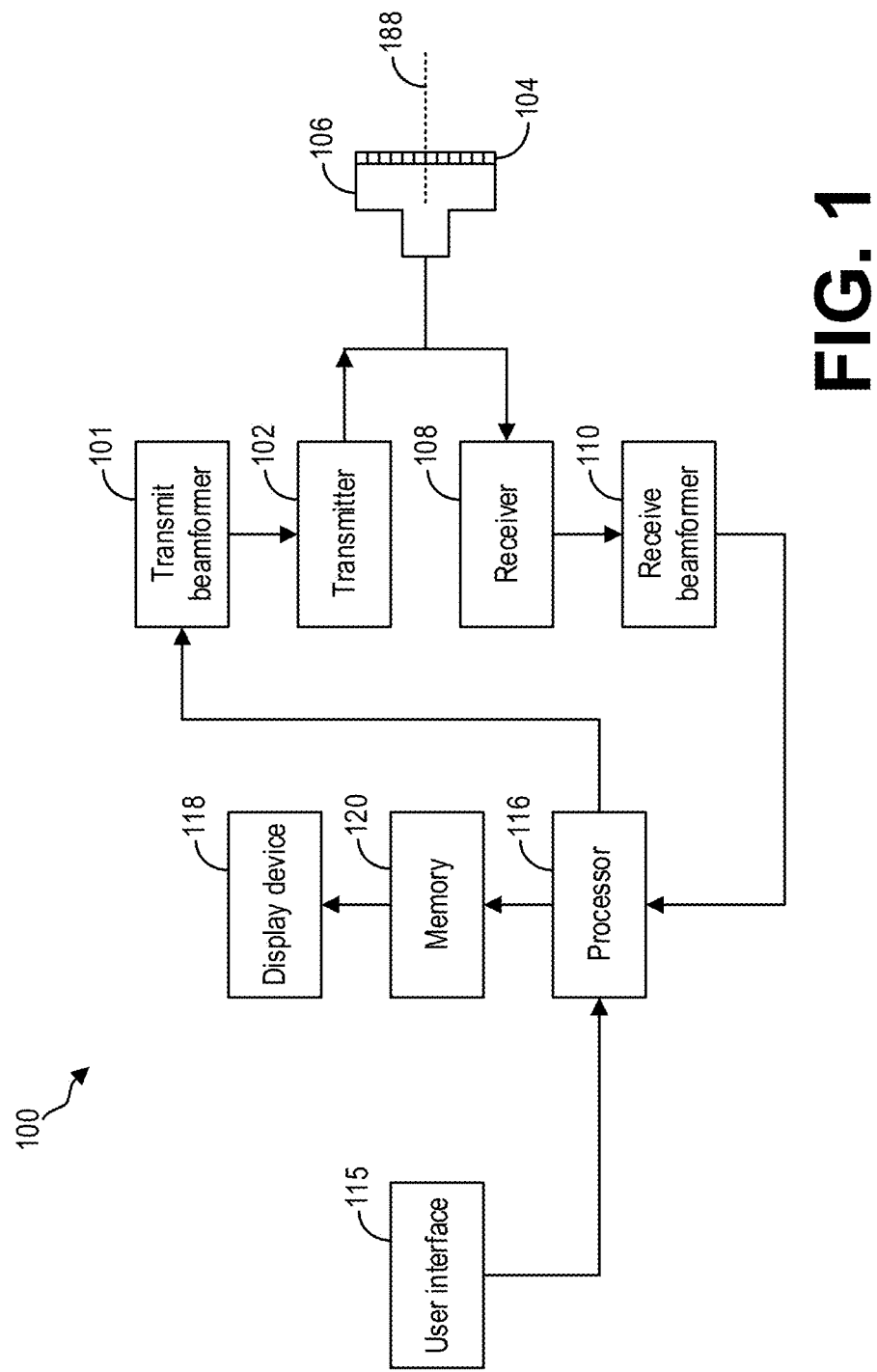
FIG. 1 shows an example ultrasound imaging system according to an embodiment.

The following description relates to various embodiments of ultrasound imaging using an ultrasound imaging system, such as the ultrasound imaging system shown in FIG. 1. In particular, systems and methods for acquiring and displaying cine loops during a periodic imaging session are provided. The periodic imaging session may include an imaging session performed on an imaging subject (e.g., a patient) where different sets of ultrasound images are acquired during different imaging periods throughout the imaging session and each set of images is saved as a cine loop for subsequent playback. The periodic imaging session may be executed during resuscitation of a patient, for example, where imaging of the patient's heart may be performed between chest compression periods. During the chest compression periods, previously acquired cine loops may be displayed on a display screen to facilitate analysis by one or more clinicians of the status of the patient's heart, in order to diagnose a condition of the heart. The previously acquired cine loops may be displayed simultaneously in different display areas of the display screen, which may allow the clinician(s) to see changes in the patient's heart over time, which may improve patient outcomes by reducing the time for diagnosis and/or increasing the accuracy of diagnosis. A method for operating an ultrasound system, such as the method depicted in FIGS. 2A and 2B, includes progressively acquiring a plurality of cine loops of an imaging subject over a periodic imaging session and simultaneously displaying each cine loop at a respective separate display area of a display screen. The displaying of the cine loops includes displaying each cine loop as the cine loop is acquired, while maintaining the display of each previously acquired cine loop. For example, during a first imaging period of the periodic imaging session, a first plurality of images are acquired with an ultrasound probe of the ultrasound system, and the first plurality of images are displayed in real time at a first display area of the display screen. An example of a display screen with a plurality of images displayed in real time at a first display area is shown in FIG. 3. Then, during a second imaging period following the first imaging period, the first plurality of images are displayed as a first cine loop at a second, different display area, while a second plurality of images are displayed at the first display area in real time (e.g., as the images are acquired), as shown in the example display screen of FIG. 4. The process may repeat itself as more cine loops are acquired. For example, as shown in FIG. 5, the second cine loop may be displayed in a third display area, next to the second display area, while display of the first cine loop is maintained. While three display areas are shown, it is understood that this number is exemplary and does not limit the number of potential display areas available for additional cine loops.

Further, during a resuscitation protocol where a clinician is performing chest compressions in an attempt to resuscitate a patient, the clinician may pause the chest compressions for a brief time period to allow imaging of the patient's heart (during which imaging period a cine loop may be acquired, as explained above). However, in some examples, the clinician may lose track of time while imaging the patient's heart and/or viewing the acquired images of the patient's heart, and as a result, an undesirably long amount of time may lapse between rounds of chest compressions. Thus, according to embodiments disclosed herein, once an imaging period during a periodic imaging mode is initiated, a countdown timer may be displayed on the display screen alongside the acquired images. The countdown timer may alert the clinician as to how many seconds are left until the next round of chest compressions should commence, which may reduce unintentional delays between rounds of chest compressions.

FIG. 1 is a schematic diagram of an ultrasound imaging system 100 in accordance with an embodiment. The ultrasound imaging system 100 includes a transmit beamformer 101 and a transmitter 102 that drive elements 104 within a transducer array or an ultrasound probe 106 to emit pulsed ultrasonic signals into a body (not shown). The ultrasound probe 106 may, for instance, comprise a linear array probe, a curvilinear array probe, a sector probe, or any other type of ultrasound probe. The elements 104 of the ultrasound probe 106 may therefore be arranged in a one-dimensional (1D) or 2D array. Still referring to FIG. 1, the ultrasonic signals are backscattered from structures in the body to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the ultrasound probe 106. The terms "scan" or "scanning" may also be used in this disclosure to refer to acquiring data through the process of transmitting and receiving ultrasonic signals. The term "data" and "ultrasound data" may be used in this disclosure to refer to one or more datasets acquired with an ultrasound imaging system.

A user interface 115 may be used to control operation of the ultrasound imaging system 100, including to control the input of patient data, to change a scanning or display parameter, to select various modes, operations, and parameters, and the like. The user interface 115 may include one or more of a rotary, a mouse, a keyboard, a trackball, hard keys linked to specific actions, soft keys that may be configured to control different functions, a graphical user interface displayed on the display device 118 in embodiments wherein display device 118 comprises a touch-sensitive display device or touch screen, and the like. In some examples, the user interface 115 may include a proximity sensor configured to detect objects or gestures that are within several centimeters of the proximity sensor. The proximity sensor may be located on either the display device 118 or as part of a touch screen. The user interface 115 may include a touch screen positioned in front of the display device 118, for example, or the touch screen may be separate from the display device 118. The user interface 115 may also include one or more physical controls such as buttons, sliders, rotary knobs, keyboards, mice, trackballs, and so on, either alone or in combination with graphical user interface icons displayed on the display device 118. The display device 118 may be configured to display a graphical user interface (GUI) from instructions stored in memory 120. The GUI may include user interface icons to represent commands and instructions. The user interface icons of the GUI are configured so that a user may select commands associated with each specific user interface icon in order to initiate various functions controlled by the GUI. For example, various user interface icons may be used to represent windows, menus, buttons, cursors, scroll bars, and so on. According to embodiments where the user interface 115 includes a touch screen, the touch screen may be configured to interact with the GUI displayed on the display device 118. The touch screen may be a single-touch touch screen that is configured to detect a single contact point at a time or the touch screen may be a multi-touch touch screen that is configured to detect multiple points of contact at a time. For embodiments where the touch screen is a multi-point touch screen, the touch screen may be configured to detect multi-touch gestures involving contact from two or more of a user's fingers at a time. The touch screen may be a resistive touch screen, a capacitive touch screen, or any other type of touch screen that is configured to receive inputs from a stylus or one or more of a user's fingers. According to other embodiments, the touch screen may comprise an optical touch screen that uses technology such as infrared light or other frequencies of light to detect one or more points of contact initiated by a user.

According to various embodiments, the user interface 115 may include an off-the-shelf consumer electronic device such as a smartphone, a tablet, a laptop, and so on. For the purposes of this disclosure, the term "off-the-shelf consumer electronic device" is defined to be an electronic device that was designed and developed for general consumer use and one that was not specifically designed for use in a medical environment. According to some embodiments, the consumer electronic device may be physically separate from the rest of the ultrasound imaging system 100. The consumer electronic device may communicate with the processor 116 through a wireless protocol, such as Wi-Fi, Bluetooth, Wireless Local Area Network (WLAN), near-field communication, and so on. According to an embodiment, the consumer electronic device may communicate with the processor 116 through an open Application Programming Interface (API).

The ultrasound imaging system 100 also includes a processor 116 to control the transmit beamformer 101, the transmitter 102, the receiver 108, and the receive beamformer 110. The processor 116 is configured to receive inputs from the user interface 115. The receive beamformer 110 may comprise either a conventional hardware beamformer or a software beamformer according to various embodiments. If the receive beamformer 110 is a software beamformer, the receive beamformer 110 may comprise one or more of a graphics processing unit (GPU), a microprocessor, a central processing unit (CPU), a digital signal processor (DSP), or any other type of processor capable of performing logical operations. The receive beamformer 110 may be configured to perform conventional beamforming techniques as well as techniques such as retrospective transmit beamforming (RTB). If the receive beamformer 110 is a software beamformer, the processor 116 may be configured to perform some or all of the functions associated with the receive beamformer 110.

The processer 116 is in electronic communication with the ultrasound probe 106. For purposes of this disclosure, the term "electronic communication" may be defined to include both wired and wireless communications. The processor 116 may control the ultrasound probe 106 to acquire data. The processor 116 controls which of the elements 104 are active and the shape of a beam emitted from the ultrasound probe 106. The processor 116 is also in electronic communication with a display device 118, and the processor 116 may process the data into images for display on the display device 118. The processor 116 may include a CPU according to an embodiment. According to other embodiments, the processor 116 may include other electronic components capable of carrying out processing functions, such as a GPU, a microprocessor, a DSP, a field-programmable gate array (FPGA), or any other type of processor capable of performing logical operations. According to other embodiments, the processor 116 may include multiple electronic components capable of carrying out processing functions. For example, the processor 116 may include two or more electronic components selected from a list of electronic components including: a CPU, a DSP, an FPGA, and a GPU. According to another embodiment, the processor 116 may also include a complex demodulator (not shown) that demodulates the RF data and generates raw data. In another embodiment the demodulation can be carried out earlier in the processing chain. The processor 116 is adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For example, an embodiment may acquire images at a real-time rate of 7-20 volumes/sec. The ultrasound imaging system 100 may acquire 2D data of one or more planes at a significantly faster rate. However, it should be understood that the real-time volume-rate may be dependent on the length of time that it takes to acquire each volume of data for display. Accordingly, when acquiring a relatively large volume of data, the real-time volume-rate may be slower. Thus, some embodiments may have real-time volume-rates that are considerably faster than 20 volumes/sec while other embodiments may have real-time volume-rates slower than 7 volumes/sec. The data may be stored temporarily in a buffer (not shown) during a scanning session and processed in less than real-time in a live or off-line operation. Some embodiments of the disclosure may include multiple processors (not shown) to handle the processing tasks that are handled by processor 116 according to the exemplary embodiment described hereinabove. It should be appreciated that other embodiments may use a different arrangement of processors.

The ultrasound imaging system 100 may continuously acquire data at a volume-rate of, for example, 10 Hz to 30 Hz. Images generated from the data may be refreshed at a similar frame-rate. Other embodiments may acquire and display data at different rates. For example, some embodiments may acquire data at a volume-rate of less than 10 Hz or greater than 30 Hz depending on the size of the volume and the intended application. The memory 120 is included for storing processed volumes of acquired data. In an exemplary embodiment, the memory 120 is of sufficient capacity to store at least several seconds' worth of volumes of ultrasound data. The volumes of data are stored in a manner to facilitate retrieval thereof according to its order or time of acquisition. The memory 120 may comprise any known data storage medium.

Optionally, embodiments of the present disclosure may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present disclosure, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. The image lines and/or volumes are stored and timing information indicating a time at which the data was acquired in memory may be recorded. The modules may include, for example, a scan conversion module to perform scan conversion operations to convert the image volumes from beam space coordinates to display space coordinates. A video processor module may be provided that reads the image volumes from a memory and displays an image in real time while a procedure is being carried out on a patient. A video processor module may store the images in an image memory, from which the images are read and displayed.

As mentioned above, the ultrasound probe 106 may comprise a linear probe or a curved array probe. FIG. 1 further depicts a longitudinal axis 188 of the ultrasound probe 106. The longitudinal axis 188 of the ultrasound probe 106 extends through and is parallel to a handle of the ultrasound probe 106. Further, the longitudinal axis 188 of the ultrasound probe 106 is perpendicular to an array face of the elements 104.

As explained previously, the ultrasound system 100 may be used during periodic imaging sessions. One example of a periodic imaging session is an imaging session carried out according to a resuscitation protocol. Resuscitation is a clinical situation in which a clinician follows a workflow/guideline that includes continuous compressions with 10 second breaks for reassessment of the patient. During these breaks the clinician or other operator uses the ultrasound probe to scan the patient's heart looking for reversible causes for cardiac arrest.

According to embodiments disclosed herein, a clock on the display screen (which is used to present the acquired images) will count down to show the clinician the time remaining until compressions need to be applied again. The timer may count-down from 10 seconds (or less, as configured by the user) to remind the clinician the maximum permissible amount of time available before chest compressions need to be resumed. The timer may initiate countdown automatically once the system detects that imaging has started or after the clinician selects a button on the probe or system to indicate that the timer needs to start. The timer may include an audible alarm in case the clinician is not focused on the screen.

Once the timer reaches 0, the clinician resumes chest compressions and the system may automatically display a slow-motion (or standard) display of the most recently acquired cine loop. This allows the clinician to identify anything he/she has missed during the 10 seconds of imaging. It also serves as an indication for the clinician as to whether the acquisition was "successful" or if additional images need to be acquired. The automatic slow motion display may enable the clinician to quickly (without having to press multiple buttons such as freeze/scroll/play/loop) play the cine loop obtained during the compression pause in order to identify any reversible causes for the cardiac arrest (e.g., cardiac tamponade, pulmonary emboli), which may be difficult to pick up in real time.

The system may automatically display the slow-motion image when the system detects that the user is no longer imaging the patient (e.g., the system would detect that the ultrasound probe is no longer in contact with the patient and then automatically display the cine loop acquired during the most-recent 10-second gap between compressions in slow motion). This may allow the clinician to focus on the image and patient and not on the ultrasound machine.

By displaying the clock/countdown timer and automatically displaying the most recently-acquired cine loop automatically, time may be saved and the clinician may be able to keep focusing on the patient and not on tapping on several buttons to display the latest cine loop. Further, the 10 second gap between compressions is a short time for the clinician to acquire and interpret the images. Currently, the clinician may have to review the images afterwards, which may involve tapping on several buttons such as freeze, play, scroll the cine bar back and forth, etc. These actions take time and distract the clinician from the patient. Further still, it may be difficult to identify cardiac pathologies and the clinician might have to play the cine loop more than once to make sure he/she did not miss anything. Playing the cine loop automatically once the clinician resumes chest compressions reduces the likelihood the user will have to deal with the ultrasound system and tap on several buttons. Playing the clip in slow motion may prevent or reduce the likelihood that the user may miss pathologies during the review.

Additionally, as will be explained in more detail below, as multiple cine loops are acquired over the course of the resuscitation protocol or other periodic imaging session, each cine loop may be displayed in a separate area of the display screen, and played back simultaneously. In doing so, changes in patient status over time may be visualized, which may reduce time to diagnosis and/or treatment, improve patient outcomes, and so forth. Further, by reducing the amount of input required from the operator to view the acquired cine loops, user interaction with the ultrasound system may be reduced, which may speed up the imaging process, reduce user frustration, and improve patient care.

Figure 2A:
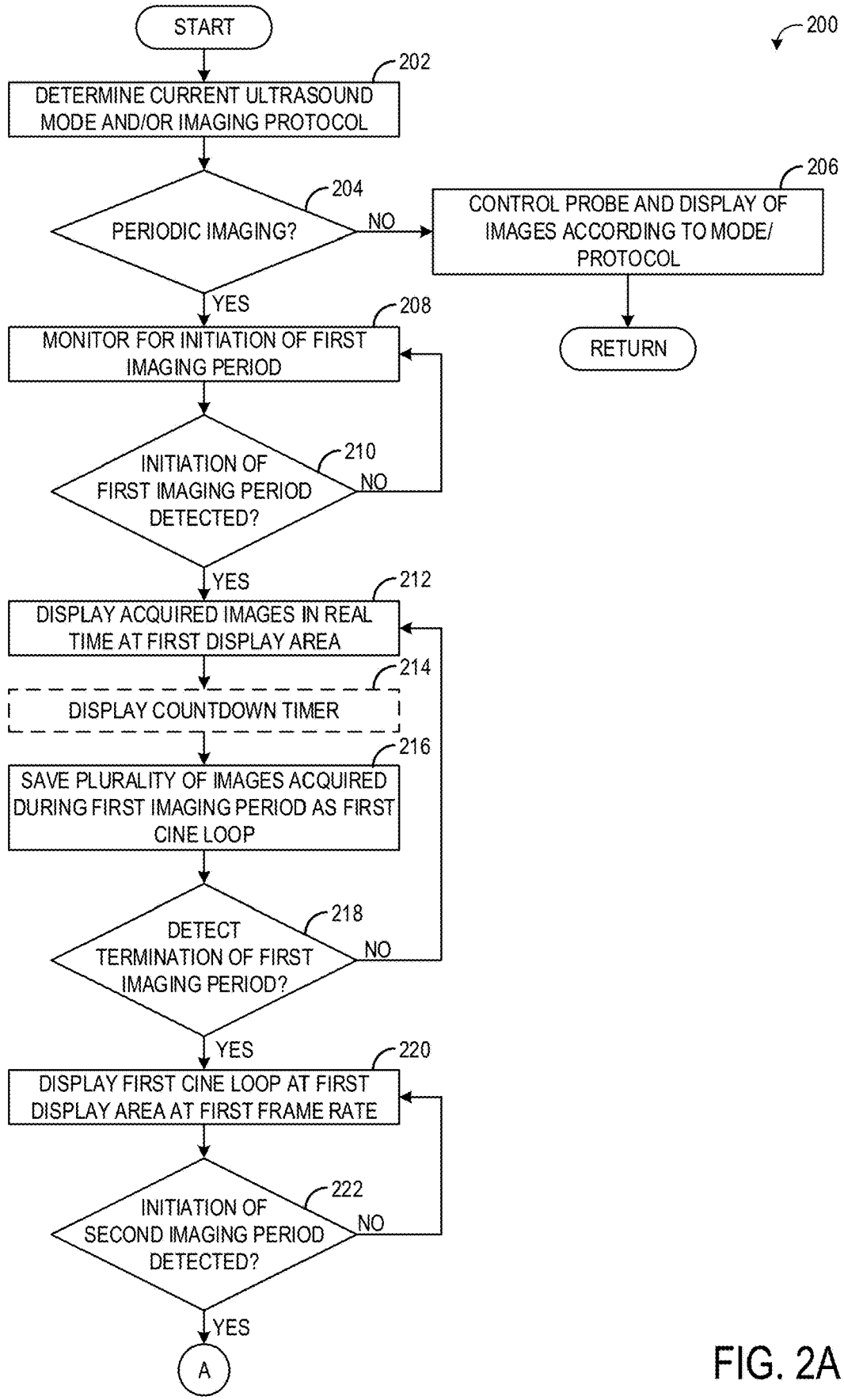
FIGS. 2A and 2B show a flow chart illustrating an example method for operating an ultrasound system in a periodic imaging session.
Figure 2B:
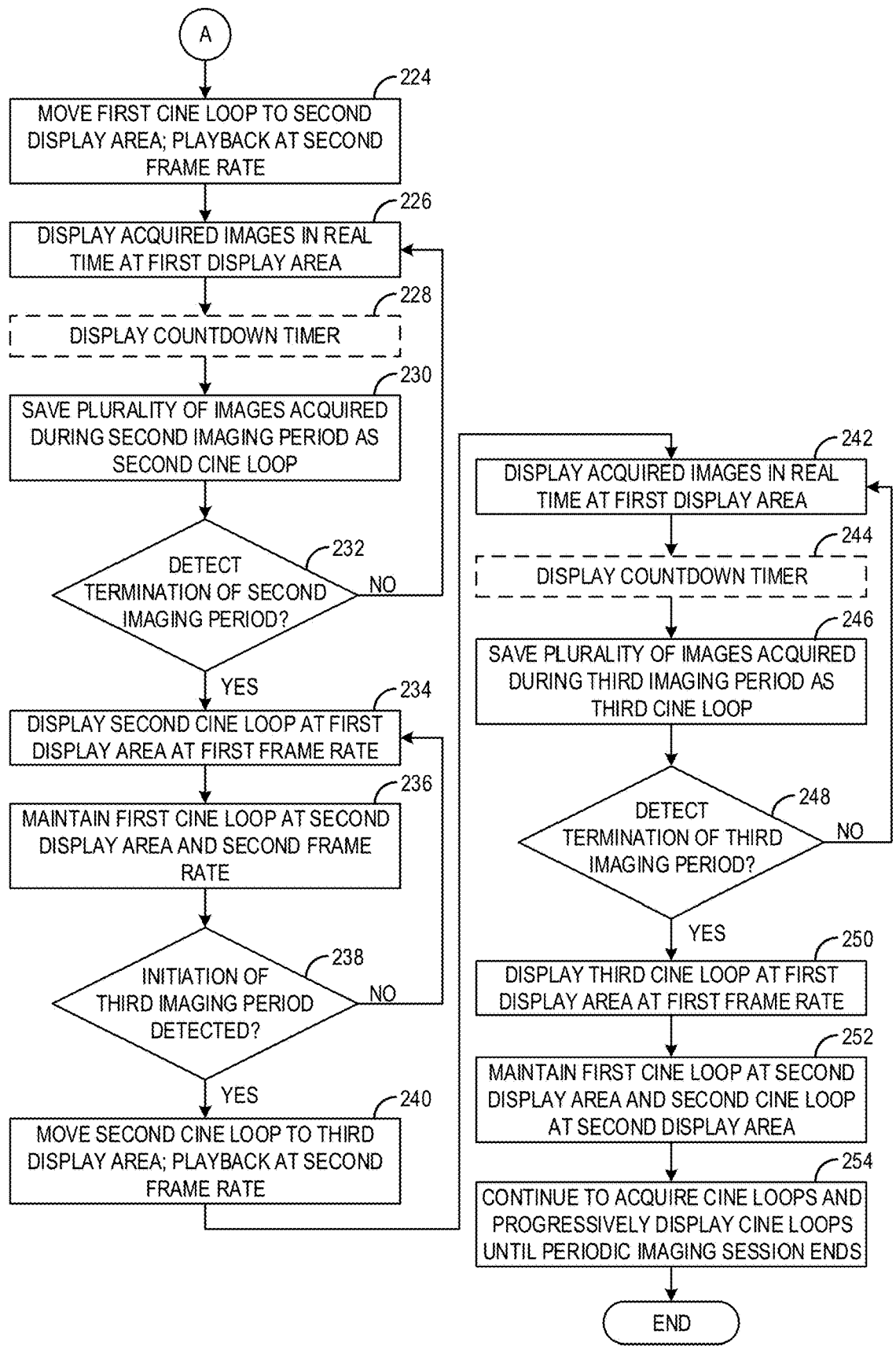
Figure 3:
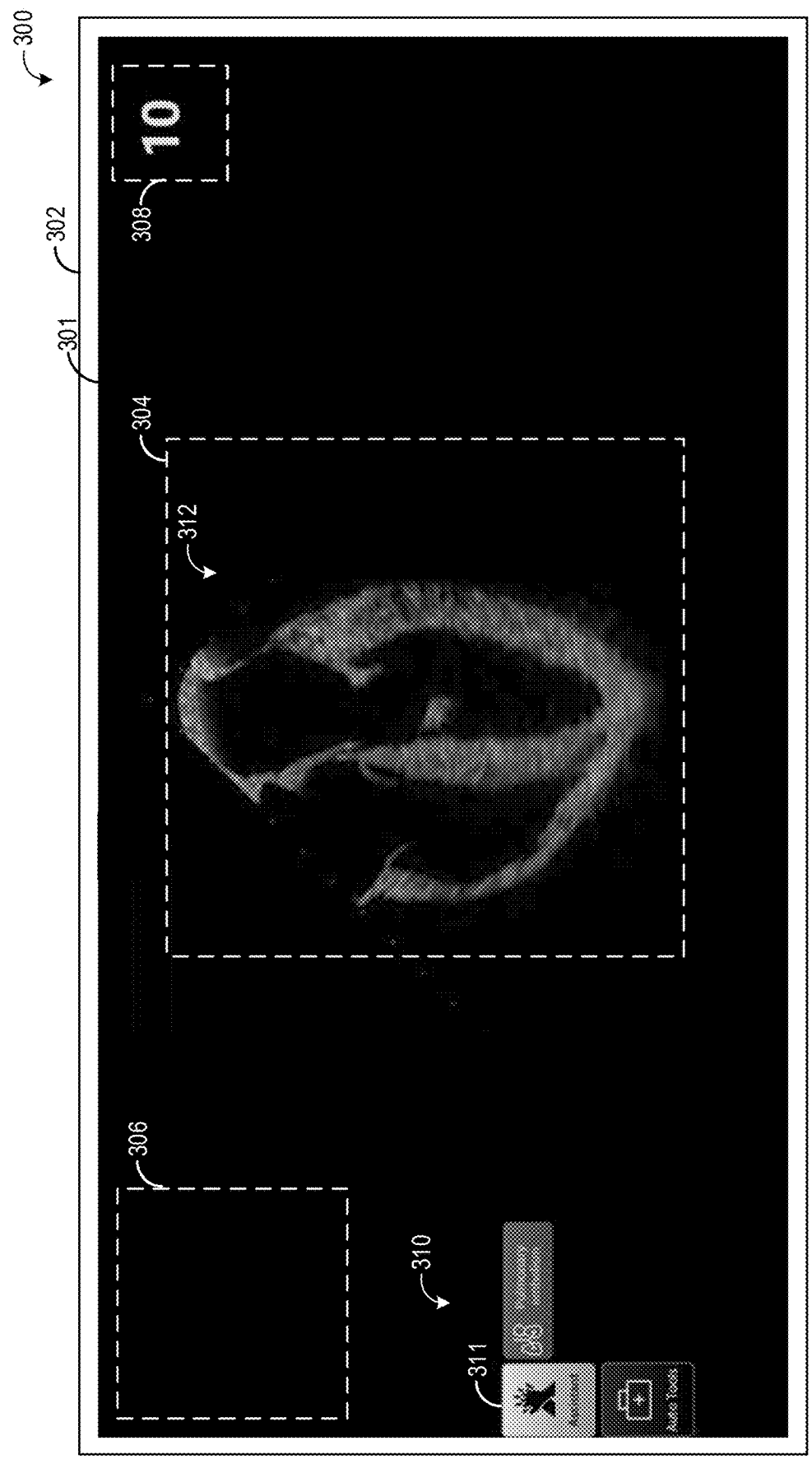
FIG. 3 shows an example display screen of an ultrasound imaging system during a first segment of a periodic imaging session.

Turning now to FIGS. 2A and 2B, a method 200 for operating an ultrasound system is shown. Method 200 is described below with regard to the systems and components depicted in FIG. 1, though it should be appreciated that method 200 may be implemented with other systems and components without departing from the scope of the present disclosure. In some embodiments, method 200 may be implemented as executable instructions in any appropriate combination of the imaging system 100, an edge device (e.g., an external computing device) connected to the imaging system 100, a cloud in communication with the imaging system, and so on. As one example, method 200 may be implemented in non-transitory memory of a computing device, such as the controller (e.g., processor 116 and memory 120) of the imaging system 100 in FIG. 1.

As shown in FIG. 2A, at 202, a current ultrasound imaging mode and/or imaging protocol is determined. The current ultrasound imaging mode may be determined according to user input received at a user interface of the ultrasound system, such as user interface 115 of FIG. 1. An operator of the ultrasound system may select an imaging mode and/or protocol via the user interface, or otherwise enter input indicating a desired ultrasound imaging mode and/or desired imaging protocol. Example ultrasound imaging modes may include B-mode imaging, Doppler imaging, M-mode imaging, and the like. Further, example ultrasound imaging protocols may include cardiac imaging protocols (e.g., echocardiograms), abdomen imaging, fetal imaging, renal imaging, and/or other anatomy-specific protocols. Additionally, some example ultrasound imaging protocols may be based on a type of procedure being performed along with or during the imaging, such as a resuscitation protocol, needle biopsy protocol, etc. The imaging mode and/or protocol may dictate which type of ultrasound probe is used, how the ultrasound probe is controlled during the imaging session (e.g., signal frequency, gain, beam focus, etc.), how the acquired image information is processed, and/or what types of images the operator is to acquire during the imaging session, which may include how the operator is to position and control the ultrasound probe during the imaging session.

At 204, method 200 includes determining if the ultrasound imaging system is operating according to a periodic imaging protocol. The determination of whether the system is operating according to a periodic imaging protocol may be based on the imaging mode and/or protocol selected by the operator of the ultrasound imaging system. For example, some imaging protocols may dictate that multiple, distinct imaging periods be performed, where a set of images are collected during each imaging period. Each set of images may then be saved as a cine loop for later playback. Example imaging protocols that include periodic imaging include resuscitation protocols and other heart monitoring protocols where cine loops are acquired to monitor a patient heart beat over a duration, such as during a stress test and during surgical procedure for valve replacement. For example, during aortic valve replacement (procedure is called TAVI) or mitral valve replacement (procedure is called MAVI), a user of the ultrasound may need to evaluate the evolution of the left ventricle ejection fraction (LVEF) before and after the valve replacement. Thus, as described herein, cine loops showing the LVEF before and after the valve replacement may be displayed in a side-by-side manner on a display screen in order to evaluate the successfulness of the surgical procedure.

If periodic imaging is not to be performed in the current ultrasound imaging protocol, method 200 proceeds to 206 to control the ultrasound probe and display acquired images according to the selected protocol/mode. Displaying the acquired images according to the selected protocol/mode may include displaying the images in a first display area of a display screen of the ultrasound system (e.g., a screen of display device 118 of FIG. 1) in real time, as the images are acquired. Further, displaying the acquired images at 206 may include only displaying any acquired cine loops in response to a user request, and only displaying acquired cine loops one at a time. Method 200 then returns.

If periodic imaging is to be performed, method 200 proceeds to 208 to monitor for initiation of a first imaging period. The first imaging period may be initiated when an operator moves the ultrasound probe out of its holder, places the ultrasound probe on the imaging subject, and/or enters an input (e.g., to the user interface or ultrasound probe) indicating that the first imaging period is to commence. Accordingly, initiation of the first imaging period may be detected based on a position of the ultrasound probe and/or received user input. In examples where the ultrasound probe is powered on prior to the ultrasound probe being positioned on the imaging subject, initiation of the first imaging period may be detected based on the images generated by the ultrasound data collected by the ultrasound probe. For example, when the probe is moved through the air and then positioned on the imaging subject, the images captured while the probe is in the air may include different image information than the images captured when the probe is positioned on the imaging subject. As an example, the images obtained while the probe is in the air may be mostly or fully dark (e.g., most or all pixels may have brightness values that are less than a threshold) as little to none of the output acoustic signals may be reflected back to the probe, while the images obtained while the probe is positioned on the imaging subject may include a higher number of pixels that have a brightness value greater than the threshold. Thus, initiation of the first imaging period may be detected based on an average pixel brightness value or a change in pixel brightness values of image(s) acquired with the ultrasound probe.

At 210, method 200 includes determining if initiation of the first imaging period has been detected. If initiation of the first imaging period has not been detected, method 200 continues to monitor for initiation of the first imaging period. If initiation of the first imaging period has been detected, method 200 proceeds to 212 to display acquired images in real time at the first display area of the display screen. The first display area may be a main display area in a center of the display screen, or other suitable portion of the display screen typically utilized for presenting real time display of images acquired by the ultrasound probe. To acquire the images, the ultrasound probe may be controlled to output ultrasound signals (e.g., via energization of the ultrasound transducers of the ultrasound probe) and receive the resultant echoes (e.g., where the output acoustic signals are backscattered from the imaging subject). The signals received by the ultrasound probe are then processed by the ultrasound system to generate the images that are output for display.

At 214, a countdown timer is optionally displayed on the display screen alongside the displayed images. The countdown timer may be displayed when the imaging protocol includes a resuscitation protocol. As explained above, during a resuscitation protocol, a clinician may perform chest compressions on the imaging subject. During a brief (e.g., 10 second) pause in the chest compressions, the clinician or other operator may control the ultrasound probe to acquire images of the imaging subject (e.g., images of the heart) in order to determine the location, type, and/or degree of damage to the heart, assess heart function, etc. To reduce inadvertent delays between rounds of chest compressions, a countdown timer may be started each time an imaging period between rounds of chest compressions is initiated. The countdown timer may be displayed on the display screen, at a different display area than the first display area where the real time images are displayed. The countdown timer may start at 10 or other suitable number (e.g., 8, 12, etc.) and count backwards to zero, over the course of 10 seconds or other corresponding amount of time. In some examples, once the countdown timer has reached zero, an alert may be output, such as an audible alert, to notify the operator that the countdown timer is finished.

At 216, a plurality of images acquired during the first imaging period are saved as a first cine loop. The plurality of images may include all the images acquired during the first imaging period, in some examples. In other examples, fewer than all images acquired during the first imaging period may be saved as the first cine loop. For example, the ultrasound system may acquire images at a first frame rate (e.g., 30 Hz) but only save half of the acquired images as the first cine loop (e.g., every other acquired image may be saved).

At 218, method 200 includes determining if termination of the first imaging period has been detected. The first imaging period may be terminated when the operator removes the ultrasound probe from the imaging subject, places the ultrasound probe back into its holder, and/or enters an input (e.g., to the ultrasound probe or the user interface) indicating that the first imaging period is complete. Accordingly, termination of the first imaging period may be detected based on a position of the ultrasound probe, average or change in pixel brightness values of acquired images, and/or received user input. If termination of the first imaging period is not detected (e.g., if the ultrasound probe is still being controlled to acquire images of the imaging subject), method 200 loops back to 214 and continues to display the acquired images in real time, save some or all of the acquired images as the first cine loop, and optionally display the countdown timer.

If termination of the first imaging period is detected, method 200 proceeds to 220 to display the first cine loop at the first display area at a first frame rate. In some examples, the first frame rate may be slower than the acquisition frame rate. By displaying the first cine loop at the first frame rate, which may be a relatively slow frame rate, the clinician(s) may be able to view the imaged anatomy in more detail than during the image acquisition process. However, in other examples, the first frame rate may be the same frame rate as the acquisition frame rate or other suitable rate that is not intentionally slowed relative to the acquisition rate. The first cine loop may be displayed as a loop, meaning that once the last frame of the loop is displayed, the first frame of the loop is displayed next, such that the images of the first cine loop are continually displayed successively, in order of acquisition. The first cine loop may be displayed/played back over the course of the entire, intervening non-imaging period unless user input pausing or stopping the playback is received.

At 222, method 200 determines if initiation of a second imaging period is detected. Initiation of the second imaging period may be detected similarly to the first imaging period, e.g., based on a position of the ultrasound probe, average or change in pixel brightness values of acquired images, and/or received user input. If initiation of the second imaging period is not detected, method 200 continues to display the first cine loop and wait for initiation of the second imaging period.

If initiation of the second imaging period is detected, method 200 proceeds to 224 (shown in FIG. 2B) to move the display of the first cine loop to a second display area, which is a different portion of the display screen than the first display area. In some examples, the first cine loop may be displayed and played back, at the second display area, at a second frame rate that is different (e.g., faster) than the first frame rate. However, in other examples, when the first cine loop is played back at the second display area, the first cine loop may be played back/displayed at the first frame rate. In some examples, the first cine loop, when displayed at the second display area, may be adjusted in size as well, relative to when the first cine loop was displayed at the first display area. For example, the second display area may be smaller in size than the first display area, and the displayed images of the first cine loop may be reduced in size to fit in the second display area.

At 226, acquired images (e.g., acquired during the second imaging period) are displayed in real time at the first display area. At 228, a countdown timer is optionally displayed, similar to the countdown timer optionally displayed at 214 and described above. At 230, a plurality of images acquired during the second imaging period are saved as a second cine loop. The plurality of images may include all of the images acquired during the second imaging period, in some examples. In other examples, fewer than all images acquired during the first imaging period may be saved as the first cine loop. For example, the ultrasound system may acquire images at a first frame rate (e.g., 30 Hz) but only save half of the acquired images as the second cine loop (e.g., every other acquired image may be saved).

At 232, method 200 includes determining if termination of the second imaging period has been detected. The second imaging period may be terminated when the operator removes the ultrasound probe from the imaging subject, places the ultrasound probe back into its holder, and/or enters an input (e.g., to the ultrasound probe or the user interface) indicating that the first imaging period is complete. Accordingly, termination of the second imaging period may be detected based on a position of the ultrasound probe, average or change in pixel brightness values of acquired images, and/or received user input. If termination of the second imaging period is not detected (e.g., if the ultrasound probe is still being controlled to acquire images of the imaging subject), method 200 loops back to 226 and continues to display the acquired images in real time, save some or all of the acquired images as the second cine loop, and optionally display the countdown timer.

If termination of the second imaging period is detected, method 200 proceeds to 234 to display the second cine loop at the first display area and at the first frame rate. The second cine loop may be displayed as a loop, meaning that once the last frame of the loop is displayed, the first frame of the loop is displayed next, such that the images of the second cine loop are continually displayed successively, in order of acquisition. The second cine loop may be displayed/played back over the course of the entire, intervening non-imaging period unless user input pausing or stopping the playback is received. At 236, display of the first cine loop is maintained at the second display area, and at the second frame rate. In this way, the most-recently acquired cine loop (the second cine loop) may be displayed at the main display area, in a larger format than the previously acquired cine loops (e.g., the first cine loop), and at least in some examples, at a slower frame rate than the previously acquired cine loops. Further, the most-recently acquired cine loop (e.g., the second cine loop) may be displayed and played back automatically and simultaneously with display and playback of the previously acquired cine loops (e.g., the first cine loop), at a different display area of the display screen.

At 238, method 200 determines if initiation of a third imaging period is detected. Initiation of the third imaging period may be detected similarly to the first and second imaging periods, e.g., based on a position of the ultrasound probe, average or change in pixel brightness values of acquired images, and/or received user input. If initiation of the third imaging period is not detected, method 200 continues to display the first cine loop and second cine loop and wait for initiation of the third imaging period.

If initiation of the third imaging period is detected, method 200 proceeds to 240 to move the display of the second cine loop to a third display area, which is a different portion of the display screen than the first display area and second display area. In some examples, the second cine loop may be displayed and played back, at the third display area, at the second frame rate (e.g., the same frame rate as the first cine loop). However, in other examples, when the second cine loop is played back at the third display area, the second cine loop may be played back/displayed at the first frame rate. In some examples, the second cine loop, when displayed at the third display area, may be adjusted in size as well, relative to when the second cine loop was displayed at the first display area. For example, the third display area may be smaller in size than the first display area, and the displayed images of the second cine loop may be reduced in size to fit in the third display area.

At 242, acquired images (e.g., acquired during the third imaging period) are displayed in real time at the first display area. At 244, a countdown timer is optionally displayed, similar to the countdown timer optionally displayed at 214 and described above. At 246, a plurality of images acquired during the third imaging period are saved as a third cine loop. Similar to the first and second cine loops, some or all of the acquired images during the third imaging period may be saved as the third cine loop.

At 248, method 200 includes determining if termination of the third imaging period has been detected. Termination of the third imaging period may be detected based on a position of the ultrasound probe, average or change in pixel brightness values of acquired images, and/or received user input. If termination of the third imaging period is not detected (e.g., if the ultrasound probe is still being controlled to acquire images of the imaging subject), method 200 loops back to 242 and continues to display the acquired images in real time, save some or all of the acquired images as the third cine loop, and optionally display the countdown timer.

If termination of the third imaging period is detected, method 200 proceeds to 250 to display the third cine loop at the first display area and at the first frame rate. The third cine loop may be displayed as a loop, meaning that once the last frame of the loop is displayed, the first frame of the loop is displayed next, such that the images of the third cine loop are continually displayed successively, in order of acquisition. The third cine loop may be displayed/played back over the course of the entire, intervening non-imaging period unless user input pausing or stopping the playback is received. At 252, display of the first cine loop is maintained at the second display area and display of the second cine loop is maintained at the third display area (with each cine loop displayed/played back at the second frame rate). In this way, the most-recently acquired cine loop (the third cine loop) may be displayed at the main display area, in a larger format than the previously acquired cine loops (e.g., the first and second cine loops), and at least in some examples, at a slower frame rate than the previously acquired cine loops. Further, the most-recently acquired cine loop (e.g., the third cine loop) may be displayed and played back automatically and simultaneously with display and playback of the previously acquired cine loops (e.g., the first and second cine loops), at a different display area of the display screen.

At 254, additional cine loops are acquired during each respective imaging period following the third imaging period, and the cine loops are progressively displayed (e.g., as they are acquired) until the periodic imaging session ends. Each time a new imaging period is initiated, the most recently acquired cine loop (which is displayed in the first display area) is moved to a different respective display area, the newly acquired images are displayed in real time at the first display area, and then the new cine loop is displayed at the first display area until initiation of a subsequent imaging period. Throughout the periodic imaging session, each acquired cine loop is displayed in its own separate display area, so that the acquired cine loops may be displayed simultaneously, in order of acquisition. The cine loops may be played back automatically (e.g., without explicit user input). During playback of the cine loops, the cine loops may be played back at the same frame rate, or one or more cine loops may be played back at different frame rates (e.g., the most recently acquired cine loop may be played at a slower frame rate than the previously acquired cine loops). Further, in some examples, each cine loop may be displayed at the same resolution. In other examples, one or more cine loops may be displayed at different resolutions. The process of acquiring and displaying the cine loops may repeat until the periodic imaging session ends, which may be detected via user input, powering down of the ultrasound probe, or other suitable mechanism. Method 200 then ends.

Thus, method 200 provides for the acquisition and display of separate cine loops of a single imaging subject (e.g., a patient) over the course of an imaging session, where each cine loop is displayed in a respective display area of a display screen. As new cine loops are acquired, previously-acquired cine loops are displayed simultaneously, to enable clinicians to monitor changes in patient status over time. The most-recently acquired cine loop may be visually highlighted, by displaying the most-recently acquired cine loop in a more prominent location (e.g., the center of the display screen), at a more prominent size (e.g., larger), and/or with other visual indicators relative to the previously acquired cine loops, which may allow the clinicians to quickly assess current versus past patient status. Further, at least in some examples, the most-recently acquired cine loop may be displayed/played back at a slower frame rate than a frame rate at which the previously acquired cine loops are played back.

As described above, each cine loop may be displayed at a separate, different display area of a display screen. For example, a first cine loop may be displayed at a top-left corner of the display screen, a second cine loop may be displayed adjacent/next to the first cine loop and to the right of the first cine loop, a third cine loop may be displayed adjacent/next to the second cine loop (e.g., to the right of the second cine loop), and so forth, such that the cine loops are displayed in a line across the display screen. However, other examples are possible, such as displaying the cine loops in two lines, in different quadrants, or other configuration. Further, each cine loop may be displayed in non-overlapping display areas. In other examples, some portions of the cine loops may overlap (e.g., a right edge of the first cine loop may be positioned under a left edge of the second cine loop). Additionally, while the different display areas have been described herein with respect to areas of a display screen, it is to be understood that in some examples, the different display areas may be different display areas of a window or graphical user interface, and the window or graphical user interface may be sized and positioned on a display screen according to user input or other parameters. In such examples, while each cine loop may be displayed in different display areas relative to each other in the window or graphical user interface, these display areas may not correspond to a fixed location of the display screen itself.

While method 200 as described above includes displaying acquired images in real time at a first display area during an imaging period, playing back the acquired images as a cine loop at the first display area during a non-imaging period following the imaging period, and then moving the cine loop to be displayed at a different, second display area responsive to initiation of a subsequent imaging period, other configurations for the display of the cine loops over the course of the imaging session are possible. For example, upon termination of the imaging period, the cine loop may be moved to the second, different display area immediately, rather than waiting for the second imaging period to commence to move the cine loop. In such a configuration, the first display area may be used exclusively to display real time images, while the cine loops may only be displayed in other, different display areas. Further, it is to be understood that when the cine loops are displayed during the periodic imaging sessions according to the disclosure, the cine loops may be automatically played back. As such, at least in some examples, displaying a cine loop may include playing back the cine loop.

Figure 4:
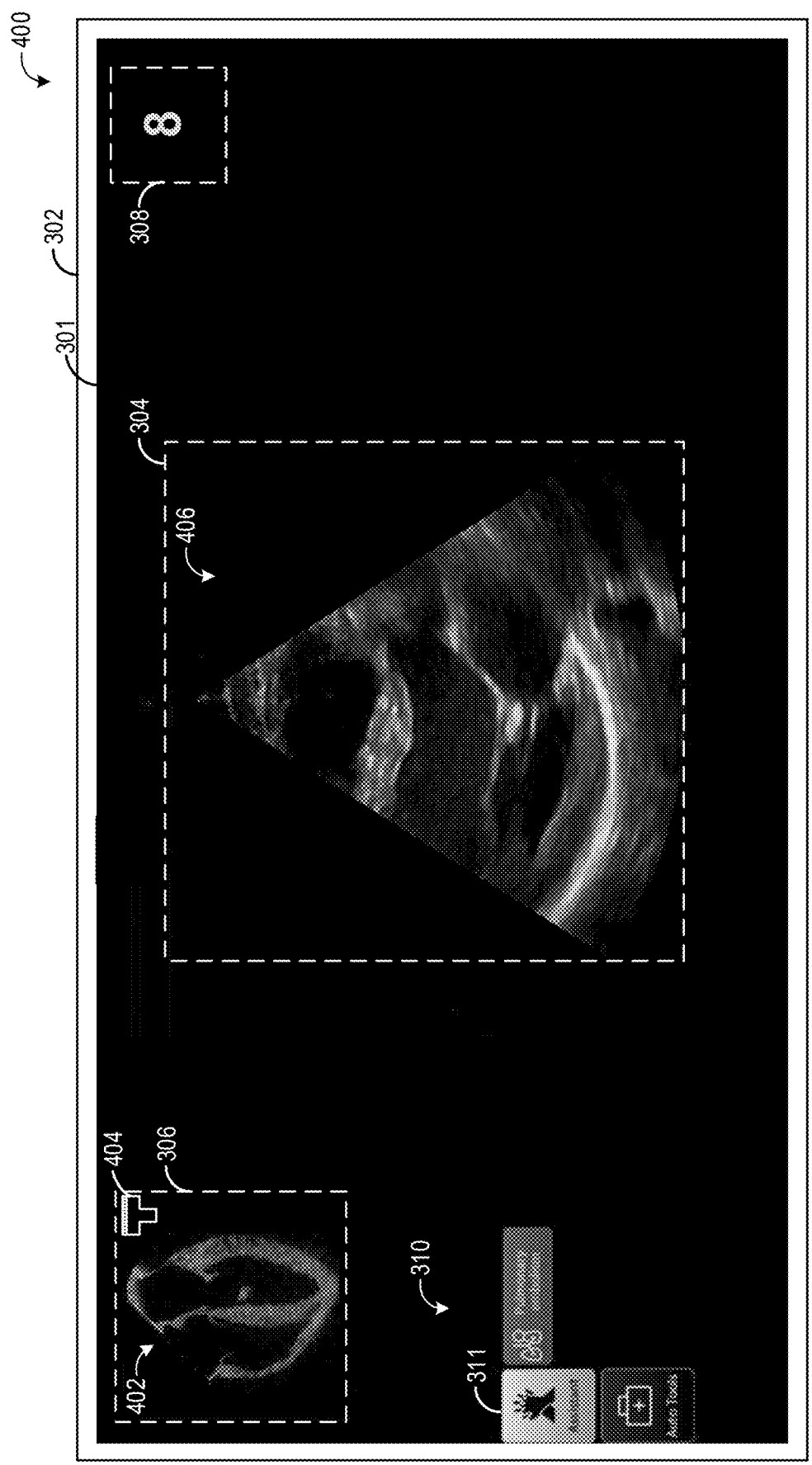
FIG. 4 shows the example display screen of the ultrasound imaging system during a second segment of the periodic imaging session.
Figure 5:
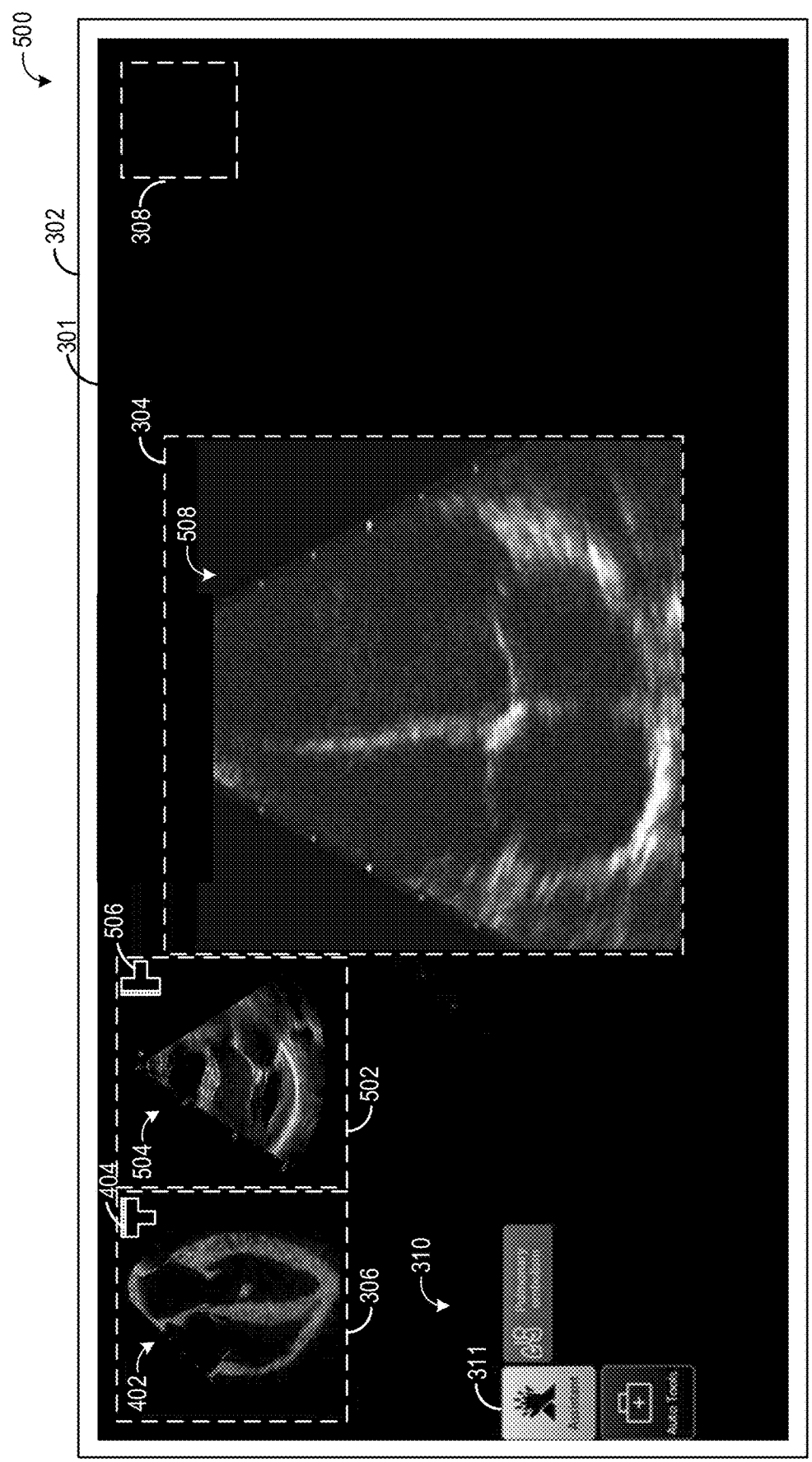
FIG. 5 shows the example display screen of the ultrasound imaging system during a third segment of the periodic imaging session.

Turning now to FIGS. 3-5, an example display screen 302 of an ultrasound system (e.g., of display device 115 of FIG. 1) is shown during various segments of a periodic imaging session. In the example shown in FIGS. 3-5, the periodic imaging session is an imaging session carried out according to a resuscitation protocol. A graphical user interface 301 is displayed on the display screen 302. As shown, the graphical user interface 301 takes up the entirety of the display area of the display screen 302. As such, the various display areas of the graphical user interface 301 described herein correspond to the display areas of the display screen 302.

FIG. 3 shows the graphical user interface 301 as displayed on the display screen 302 during a first segment 300 of the periodic imaging session. The graphical user interface 301 includes multiple display areas, including a first display area 304, a second display area 306, and a timer display area 308. Further, the graphical user interface 301 includes a plurality of icons 310. The plurality of icons 310 includes a resuscitation icon 311, which indicates to the operator and/or other clinicians that the resuscitation protocol is currently being executed by the ultrasound system. The other icons may include a findings icon (indicating that an operator has entered a clinical finding, herein a pulmonary embolism, to a medical record of the patient being treated by the clinician (s) and imaged via the resuscitation protocol) and an auto tools icon, which may be a user interface control button that when selected causes the display of a user interface menu or other suitable additional icons. Other graphical user interface elements may also be displayed via the graphical user interface 301, such as patient information, image acquisition parameters, and other user interface control buttons/icons.

The first segment 300 of the periodic imaging session may include a first imaging period where images of the patient are acquired via the ultrasound probe of the ultrasound system. The acquired images are displayed in real time at the first display area 304, such as image 312. Some or all of the images acquired during the first imaging period are saved as a first cine loop for later playback (which will be shown in FIGS. 4 and 5 and described below). As no other cine loops have been previously acquired, any other display areas of the graphical user interface 301 reserved for cine loops (e.g., the second display area 306) are not currently displaying a cine loop. A countdown timer is displayed in the timer display area 308. As explained above, the countdown timer may count backwards (e.g., from 10) over a suitable duration (e.g., 10 seconds) in order to notify one or more clinicians and/or the operator of the ultrasound system when to stop imaging the patient and resume chest compressions on the patient.

FIG. 4 shows the graphical user interface 301 as displayed on the display screen 302 during a second segment 400 of the periodic imaging session. The second segment 400 of the periodic imaging session may include a second imaging period following the first imaging period where image acquisition via the ultrasound probe is occurring. The second imaging period may be performed after an intervening non-imaging period where image acquisition was paused to allow patient chest compression to occur, for example. During the non-imaging period, the first cine loop may be displayed in the first display area 304. However, upon detecting initiation of the second imaging period, the first cine loop is moved from the first display area 304 to the second display area 306. Accordingly, as shown in FIG. 4, the first cine loop 402, which is comprised of the images acquired during the first imaging period, such as image 312, is displayed at the second display area 306. As appreciated from FIGS. 3 and 4, when the first cine loop is moved to the second display area 306, the first cine loops is reduced in size, relative to the size of the displayed acquired images displayed in the first display area 306 during the first imaging period.

In some examples, additional information about the acquisition of the first cine loop may be displayed in the second display area 306. For example, as shown, a probe orientation icon 404 is displayed, which may indicate a net or average orientation of the ultrasound probe during the acquisition of the first cine loop. Such an icon may be helpful if different cine loops are acquired at different probe orientations, as the icon may quickly identify the probe orientation and hence potential anatomical sections imaged in the cine loop. The determination of the probe orientation may be based on one or more sensors (e.g., accelerometers, gyroscopes, etc.) positioned in or on the ultrasound probe, and may be relative to a default orientation of the ultrasound probe, identified anatomical features of the patient, or other suitable parameter. The additional information may additionally or alternatively include a time stamp (e.g., indicating when the first cine loop was acquired), identified anatomical features imaged via the cine loop (e.g., which may be determined via user input or determined automatically via object recognition performed on images of the cine loop), and/or other information relevant to the cine loop.

During the second imaging period, a second plurality of images are acquired via the ultrasound probe, which are displayed in real time at the first display area 304. For example, as shown, an image 406 is displayed in the first display area 304. A countdown timer is displayed in the timer display area 308. As shown in FIG. 4, the countdown timer is at 8, which may indicate that the operator has 8 seconds left during which the operator may acquire images of the patient, before chest compressions are to resume.

FIG. 5 shows the graphical user interface 301 as displayed on the display screen 302 during a third segment 500 of the periodic imaging session. The third segment 500 of the periodic imaging session may include a non-imaging period following a third imaging period. Thus, no countdown timer is displayed in the timer display area 308. During the third imaging period (not shown), a third cine loop 508 may be acquired via the ultrasound probe, and during acquisition of the third cine loop 508, the images forming the third cine loop are displayed in real time (e.g., as the images are acquired and without intentional delay) at the first display area 304. When the third imaging period is initiated, the second cine loop 504, acquired during the second imaging period, is moved from the first display area 304 to a third display area 502. Thus, as shown, the second cine loop 504 is displayed in the third display area 502. The third display area 502 is adjacent to the second display area 306. As used herein, "adjacent" may include an edge of the display area being within a threshold distance (e.g., within 3-5 cm) of a nearest edge of another display area, and without any other cine loop display areas disposed in between. The third display area 502 may be the same size and shape as the second display area 306, and may be aligned with the second display area 306 along a common axis (e.g., a longitudinal axis of the graphical user interface 301). The second and third display areas do not overlap in the example shown in FIG. 5. Similar to the second display area 306, the third display area 502 may include a probe orientation icon 506 and/or additional or alternative displayed information, such as a timestamp of when the second cine loop was acquired. As appreciated from FIG. 5, the second cine loop 504 was acquired at a different probe orientation than the first cine loop 402.

Once the third imaging period has terminated, the images acquired during the third imaging period are displayed as the third cine loop 508 at the first display area 304. The third cine loop 508 may be displayed and played back while the first cine loop 402 and the second cine loop 504 are displayed and played back. In this way, multiple different cine loops, acquired at different times over the course of a single imaging session on the same imaging subject, may be displayed simultaneously. The most recently acquired cine loop (e.g., the third cine loop 508) may be displayed at a more prominent location (e.g., at the first display area 304, which may be in the middle of the graphical user interface 301) and at a more prominent size (e.g., larger) than the previously acquired cine loops (e.g., the first cine loop 306 and the second cine loop 502). Further, in some examples, the most recently acquired cine loop (e.g., the third cine loop 508) may be played back at a slower frame rate than the previously acquired cine loops (the first cine loop 306 and the second cine loop 502). For example, the most recently acquired cine loop may be played back at half the frame rate of the previously acquired cine loops.

In some examples, the periodic imaging session may include a plurality of imaging periods, such as three, four, five, or more imaging periods. As explained above, a separate cine loop may be acquired during each imaging period, and each cine loop may be displayed simultaneously on the same graphical user interface/display screen. However, as appreciated by FIG. 5, if too many cine loops are displayed at the same time, the available display area on the display screen may become limited. Thus, in some examples, after a threshold number of cine loops have been acquired (e.g., five), the earliest cine loops (e.g., the first cine loop) may be removed from the graphical user interface/display screen. In this way, only the most recent five (or other suitable number) of cine loops may be displayed. Additionally or alternatively, as additional cine loops are acquired and displayed, the displayed cine loops may be shrunk in size, moved around, made to overlap, or other adjustments to the display of the cine loops may be performed, in order to accommodate all the cine loops on the same graphical user interface/display screen. Further, in some examples, upon terminating an imaging period, an operator may enter an input (e.g., via a user interface or to the ultrasound probe) indicating whether the acquired cine loop should be displayed. For example, the operator may determine that no useful information was obtained during the most recent imaging period, and thus the operator may enter an input indicating that the most recently acquired cine loop should not be displayed. By doing so, only the cine loops determined by the operator to be useful in diagnosing and/or treating the patient may be displayed. Further, such a configuration may improve user interaction with the graphical user interface (e.g., reduce the amount of user input actions required to view desired cine loops, reduce clutter on the graphical user interface, and improve visualization of desired images/cine loops), thus facilitating more rapid imaging, reduced time to patient diagnosis, and increased user satisfaction.

Thus, as described herein, during a periodic imaging session such as a patient resuscitation protocol, a clinician may alternate between non-imaging periods (e.g., where the clinician applies chest compressions to a patient) and imaging periods where the patient is imaged with an ultrasound probe. During the resuscitation protocol, the clinician may only have a 10 second (or other suitable amount of time) window to image the patient before the chest compressions are to be started up again. Thus, a countdown timer or alarm may be provided while the clinician is imaging to make sure that the clinician resumes chest compressions at the appropriate time.

As the clinician acquires images through multiple imaging/non-imaging cycles, the ultrasound system will acquire a plurality of cine loops. (Each cine loop is a series of ultrasound frames acquired over a period of time.) As described herein, the progression of cine loops are displayed on the display screen as they are acquired. For example, a first cine loop may be displayed in the upper left side of the screen, the next cine loop may be displayed to the right of the first one, etc. Accordingly, over time, a series of cine loops may be displayed on the screen, each corresponding to a different acquisition time between non-imaging periods (e.g., compressions). The cine loops may be acquired during a patient resuscitation or other type of procedure that would involve acquiring multiple cine loops at different times.

The system may display the progression of cine loops over time. All the cine loops would play back on the same time. The cine loops would not necessarily be synchronized, but could be synchronized if desired. By displaying the cine loops at the same time and on the same screen, the clinician (s) may more easily see changes in the patient over time. In some examples, the most-recently acquired cine loop may be visually indicated (such as by displaying that cine loop in a larger format, or highlighting it in some other way).

A technical effect of simultaneously displaying each cine loop at a respective separate display area of a display, including displaying each cine loop as that cine loop is acquired, while maintaining display of each previously acquired cine loop, is increased imaging speed, reduced time to patient diagnosis, reduced amount of user input to the ultrasound system, and increased user satisfaction with the ultrasound imaging system.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   operating an ultrasound display of a system during a periodic imaging session, the session including:
   during a first segment of the periodic imaging session:
   acquiring, with an ultrasound probe, a first set of images of an imaging subject during a first imaging period;
   displaying the first set of images at a first display area of a display; and
   responsive to detecting initiation of the first imaging period, displaying a countdown timer on a third display area of the display to alert a user a time before chest compressions are to be performed, the countdown timer counting down from a value configured by the user;
   during a non-imaging period following the first imaging period, displaying the first set of images at the first display area of the display at a first frame rate; and
   during a second segment of the periodic imaging session:
   detecting initiation of a second imaging period, different that the first imaging period;
   acquiring, with the ultrasound probe, a second set of images of the imaging subject during the second imaging period; and
   responsive to detecting initiation of the second imaging period, moving display of the first set of images from the first display area to a second display area of the display;
   upon the first set of images being moved to the second display area, displaying the first set of images at a second, different frame rate;
   displaying, in real-time, the second set of images at the first display area of the display, different than the second display area, while maintaining display of the first set of images at the second display area; and
   not displaying the countdown timer on the third display area of the display, wherein the second imaging period follows the first imaging period.

2. The method of claim 1, further comprising automatically initiating count-down via the countdown timer once the system detects that imaging has started.

3. The method of claim 1, further comprising once the countdown timer reaches 0, automatically displaying a slow-motion or standard display of a most recently acquired cine loop.

4. The method of claim 1, further comprising during the first imaging period, displaying the first set of images in real time.

5. The method of claim 1, wherein the third display area is located adjacent to the first display area.

6. A system, comprising:
   an ultrasound probe;
   a display; and
   a processor configured with instructions in non-transitory memory that when executed cause the processor to:
   during periodic imaging sessions carried out according to a resuscitation protocol comprising compressions with breaks for reassessment where the ultrasound probe is operated to scan a heart of a patient:
   acquire, with the ultrasound probe, a first cine loop of an imaging subject during a first imaging period;
   during a non-imaging period following the first imaging period, display the first cine loop at a main display area of the display at a first frame rate;

detect initiation of a second imaging period, and in response, move display of the first cine loop from the main display area to a first display area of the display;

upon the first cine loop being moved to the first display area, display the first cine loop at a second, different frame rate;

acquire, with the ultrasound probe, a second cine loop of the imaging subject during the second imaging period following the first imaging period;

display a countdown timer on the display that presents acquired images;

count down the countdown timer to show time remaining until compressions are to be applied, including counting down to zero;

initiate count-down automatically once the system detects that imaging has started;

once the countdown timer reaches zero, automatically display a most recently acquired cine loop; and when the system detects that a user is no longer imaging the patient, automatically display the most recently acquired cine loop;

simultaneously display the first cine loop at the first display area of the display and the second cine loop at a second display area of the display.

7. The system of claim 6, wherein the first cine loop comprises a first plurality of images of the imaging subject acquired with the ultrasound probe during the first imaging period and the second cine loop comprises a second plurality of images of the imaging subject acquired with the ultrasound probe during the second imaging period.

8. The system of claim 6, wherein the second display area is adjacent the first display area, and where the first display area and second display area do not overlap.

9. The system of claim 6, wherein the main display area is larger than the first display area and the second display area.

10. The system of claim 6, wherein during the first imaging period, each image forming the first cine loop is displayed in the main display area in real time as each image is acquired.

11. A method, comprising:

during periodic imaging sessions carried out according to a resuscitation protocol comprising compressions with breaks for reassessment where an ultrasound probe is operated to scan a patient heart of an imaging subject:

progressively acquiring a plurality of cine loops of the imaging subject over a periodic imaging session;

simultaneously displaying each cine loop at a respective separate display area of a display, including displaying acquired images of each cine loop as that cine loop is acquired, displaying each cine loop in a main display area of the display at a first frame rate during a non-imaging period following acquisition of that cine loop, and maintaining display of each previously acquired cine loop in a first display area of the display at a second, different frame rate;

display a countdown timer on the display that presents acquired images;

count down the countdown timer to show time remaining until compressions are to be applied, including counting down to zero;

initiate count-down automatically in response to detecting that imaging has started; and once the countdown timer reaches zero, automatically display a most recently acquired cine loop.

12. The method of claim 11, further comprising initiating the periodic imaging session in response to user input.

13. The method of claim 12, wherein the user input includes selection of the resuscitation protocol.

14. The method of claim 11, further comprising upon a threshold number of cine loops being displayed on the display, adjusting display of one or more previously acquired cine loops.

15. The method of claim 14, wherein adjusting display of one or more previously acquired cine loops includes reducing a display size of the one or more previously acquired cine loops.

* * * * *